United States Patent [19]

Bourguignon et al.

[11] Patent Number: 5,359,198
[45] Date of Patent: Oct. 25, 1994

[54] SCINTILLATION DEVICE USABLE FOR MEASURING ATTENUATION THROUGH TRANSMISSION TOMOGRAPHY

[75] Inventors: Michel Bourguignon, Sceaux; Marie-Michèle Vassiliou, Paris; Francois de la Barre, Sevres, all of France

[73] Assignees: Sopha Medical; Commissriat a l'Energie Atomique, both of Paris, France

[21] Appl. No.: 820,613

[22] Filed: Mar. 27, 1992

[30] Foreign Application Priority Data

Jul. 28, 1989 [FR] France .................. 89 10225

[51] Int. Cl.$^5$ .......................... G01T 1/166; G01T 1/20
[52] U.S. Cl. .................. 250/363.07; 250/363.02; 250/363.04; 378/55; 378/195
[58] Field of Search ............ 250/363.02, 363.04, 250/363.07; 378/53, 55, 146, 177, 195, 151, 152, 153

[56] References Cited

U.S. PATENT DOCUMENTS

| | | | |
|---|---|---|---|
| 4,151,416 | 4/1979 | Richey et al. | 250/363.07 |
| 4,212,061 | 7/1980 | Knoll et al. | 250/363.07 |
| 4,216,381 | 8/1980 | Lange | 250/363.05 |
| 4,220,861 | 9/1980 | Colombo et al. | 20/363.05 |
| 4,223,221 | 9/1980 | Gambini et al. | 250/363.07 |
| 4,323,977 | 4/1982 | Arseneau | 250/363.07 |
| 4,424,446 | 1/1984 | Inbar et al. | 250/363.07 |
| 4,429,226 | 1/1984 | Inbar | 250/363.07 |
| 4,774,411 | 9/1988 | Span | 250/363.05 |
| 4,780,823 | 10/1988 | Stoub et al. | 250/363.07 |
| 4,788,429 | 11/1988 | Wilson | 378/53 |
| 5,047,641 | 9/1991 | Besseling et al. | 250/363.05 |
| 5,055,687 | 10/1991 | Ichihara | 250/365.04 |
| 5,105,086 | 4/1992 | Pierfite | 250/363.05 |
| 5,172,695 | 12/1992 | Cann et al. | 378/54 |
| 5,185,529 | 2/1993 | Smith et al. | 250/363.07 |
| 5,228,068 | 7/1993 | Mazess | 378/54 |

FOREIGN PATENT DOCUMENTS

| | | |
|---|---|---|
| 0092437 | 10/1983 | European Pat. Off. . |
| 3236082 | 3/1984 | Fed. Rep. of Germany ...... 378/152 |
| 0092974 | 6/1983 | Japan ............................ 250/363.04 |
| 0180477 | 10/1984 | Japan ............................ 250/363.05 |
| 0186300 | 10/1989 | Japan .................................. 378/152 |

OTHER PUBLICATIONS

Park, Chan Hee et al., "Use of Simultaneous Transmission-Emission Scanning in the Diagnosis of Pericardial Effusion", Journal of Nuclear Medicine vol. 13 No. 6, pp. 347-348, Jun. 1972.

Bailey, Dale L. et al., "Improved SPECT Using Simultaneous Emission and Transmission Tomography", Journal of Nuclear Medicine, vol. 28 No. 5, pp. 844-851, May 1987.

The Journal of Nuclear Medicine, vol. 27, No. 5, May 1986, (New York, N.Y., US) J. A. Malko et al.: "SPECT Liver imaging using a iterative attenuation correction algorithm and an external flood source", pp. 701-705.

Primary Examiner—Paul M. Dzierzynski
Assistant Examiner—Drew A. Dunn
Attorney, Agent, or Firm—Oblon, Spivak, McClelland, Maier & Neustadt

[57] ABSTRACT

A gamma camera is provide, that can be used to measure the coefficient of attenuation of the gamma radiation in a body studied by means of a gamma camera normally made to study the effects of gamma radiation emitted by markers injected into the body. To this end, the collimator is removed from this gamma camera, and it is replaced by a ring and by an arm to which there is fixed a chamber designed to contain a radioactive point source external to the body. It is shown that it is thus possible to obtain images in transmission very swiftly. These images are useful for the correction of normal emission images.

8 Claims, 2 Drawing Sheets

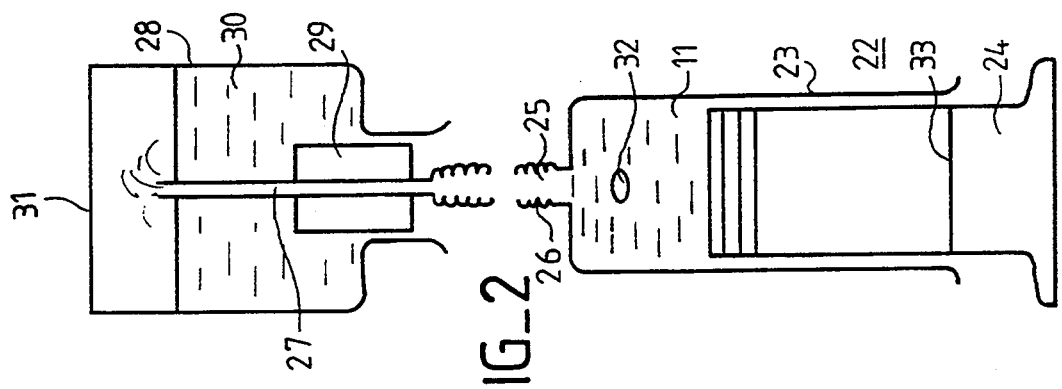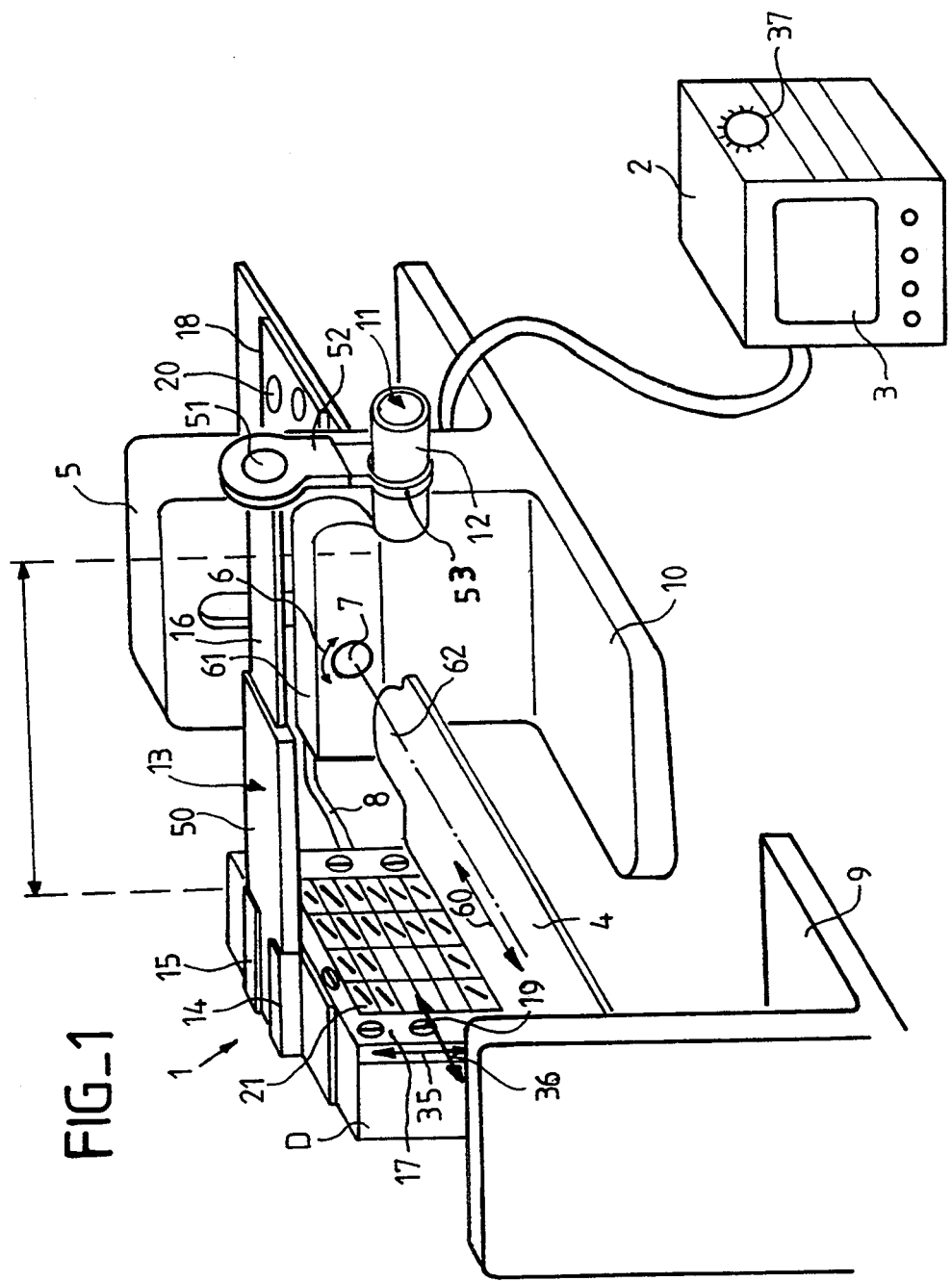

FIG_3
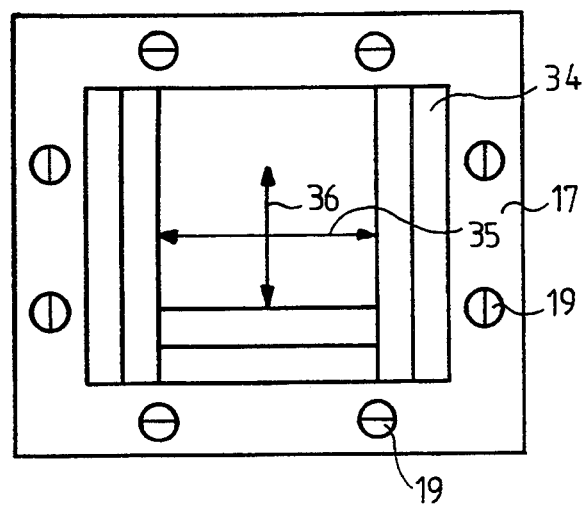
FIG_4
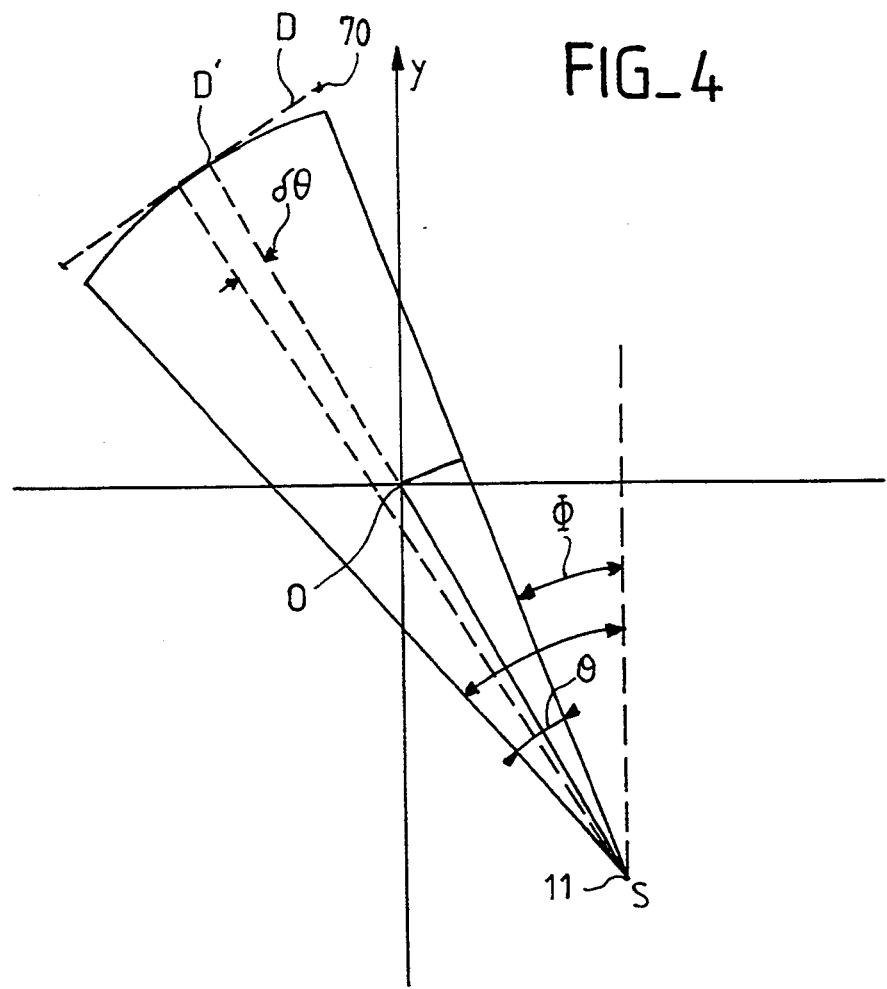

SCINTILLATION DEVICE USABLE FOR MEASURING ATTENUATION THROUGH TRANSMISSION TOMOGRAPHY

BACKGROUND OF THE INVENTION

1. Field of the Invention

An object of the present invention is to provide scintillation device that can be used to measure attenuation by emission tomography. It can be applied more particularly in the medical field or in association with a gamma camera used in a standard way, and provides for more precise knowledge of the internal structures revealed by an emission tomography examination carried out by means of this gamma camera.

2. Description of the Prior Art

An emission tomography examination carried out by means of a gamma camera comprises the injection, into a body to be examined, of a radioactive marker. In the medical field, the marker, for example Technetium, is injected, in the form of a dilution, into the patient's body. While moving in his body, the radioactive marker produces a measurable radioactive phenomenon. The radioactive phenomenon essentially comprises the emission of gamma rays.

To measure this radioactive phenomenon, a gamma camera or scintillation camera provided with a plane scintillator crystal is used. A gamma camera essentially has a stand to support a detector surmounted by the scintillator crystal. The gamma camera also has a control and processing panel. The detector comprises an arrangement of photomultiplier tubes to produce electrical signals corresponding to detected scintillations. The scintillator absorbs the gamma radioactive radiation by photoelectrical effect. It transmits light radiation detected downline by the array of the photomultiplier tubes of the detector. The tubes are associated with computing means. These computing means can be used to determine the coordinates of a locus of interaction of the gamma radiation in the scintillator.

Since the radioactive emissions in the body are omnidirectional, the only way to do this localization efficiently is to interpose a collimator between the body and the scintillator. This collimator lets through radioactive radiation only in a chosen direction.

With examinations such as these, it is possible to produce projected images. If the gamma camera is made to rotate about the body of the patient while the radioactive phenomenon occurs (during an examination period of about half an hour), it is possible to acquire a certain number of parallel type projections with which section images can be reconstructed according to tomography methods of a known type. The projections are of a parallel type because the collimator lets through rays in only one direction perpendicular to its plane.

The above acquisition mode has, however, one drawback: before exciting the scintillator, the gamma rays emitted by the internal structures of the body have to cross other regions of the body and thereby undergo a corresponding attenuation. This disturbs the acquisition of the data and the exactness and precision of the data.

Many attempts have been made to take this attenuation into account without actually measuring it. However, the methods proposed for this purpose have proved to be of little benefit and, to date, the real measurement of the attenuation by transmission tomography appears to be the only approach that can be envisaged.

It is possible, for example, to consider measuring radiological attenuation by using the measurements of tomodensitometry proposed in modern tomodensitometers using X-rays.

However, this approach has two drawbacks. Firstly, the patient has to be moved from one machine to another. It can never be certain that he will take up the same position in the second machine as in the first one. It becomes difficult to compare or transpose the measurements. Moreover, the energies of the radiation used in each case differ from each other. It is X-radiation that is used in tomodensitometry and gamma radiation in the scintillation device, and the coefficients of attenuation measured all depend on the energy of the radiation absorbed.

One method of measuring the attenuation by transmission tomography, using a rotational gamma camera provided with its collimator and a large external radioactive plane source, has been tested with a certain degree of success.

However, there are several serious drawbacks that restrict the use of this method in practice. Firstly, the additional acquisition time (acquisition for the measurement of the attenuation by transmission) is too long. Indeed, it lasts about 30 minutes. Furthermore, it is difficult to prepare a plane radioactive source in the sense that it is never possible to be assured of the homogeneity of the emission of the different parts of the source. A plane radioactive source is also difficult to manipulate because of its weight. Finally, and above all, it gives rise to a permanent irradiation that is unacceptable to those persons who have to use it. A technique of this kind has, for example, been described in the article by Malko J. A. & al., "SPECT Liver Imaging using an Iterative Correction Algorithm and an External Flood Source" in *Journal of Nuclear Medecine*, 27:701–705, 1986.

Another method has been proposed associating a point gamma source with a gamma camera without collimator. It has been described by Deconinck F. & al. in "Computerized Transmission Densitography and Tomography with a Gamma Camera", INSERM conference, INSERM 1979, vol. 88, pp. 245–256. In this method, a point source is placed at two meters from a gamma camera in a horizontal plane. The patient is brought closer in a rotating chair between this source and this gamma camera. The chair rotates about a vertical axis. The distance of two meters is a minimum distance to allow the gamma radiation emitted by the point source to be considered as a radiation parallel to the position of the irradiated body. The different projections are acquired by making the chair rotate.

This last-named technique has two drawbacks. Firstly, the distance at which the source is located is such that it becomes impossible to envisage the production of a structure that is rigid enough to enable the gamma camera (which is heavy) and the source to be kept in a relationship of correspondence when this assembly is rotating about the body, without its becoming necessary to undergo vibrations. Furthermore, the volumes needed for medical examination rooms would be off standards. Besides, this impossibility dictates a situation where it is the patient who has to be made to move in relation to the camera, and this is impossible in certain cases, especially when the patients are physically weak and are incapable of taking a vertical or seated position. It is necessary to take into account a situation where the patient slumps down in the course of time. This causes the interpenetration of the sections acquired and thus falsifies their reconstruction.

The disadvantage of bringing the source closer to the gamma camera to thus constitute a structure that can be manipulated around the patient is that it means losing the parallel character of the radiation which consequently bars the use of known algorithms for the reconstruction of the attenuation images acquired.

It is an object of the invention to overcome these drawbacks by using, a point source positioned in correspondence with and in the vicinity of the gamma camera. In practice, the proximity is less than one meter: in a preferred example, it is 70 cm.

Then, to resolve the problems of conical geometry prompted by this proximity, the following operations are performed: a weighting operation corresponding to an arrangement of all the conical projections thus obtained in a set of parallel projections, and a log standardization by the intensity of the source. Under these conditions, it is possible to have a nearby point source available, the efficiency of which is further increased because of its greater proximity to the body. In this case, then, no collimator is used, making the gamma camera 300 to 500 times more sensitive than it would be if it had a collimator. Under these conditions, it is possible to reduce the acquisition times for the measurement of the attenuation in transmission to about one minute: this is the time needed to acquire 64 projections for a duration of one second for each projection.

The equipment that can be used is then a standard type of equipment: the same as the one used for transmission tomography (i.e. tomography that involves revealing the presence of markers in the body). In the invention, given the fact that a standard type of equipment is used, the collimator which has been removed is judiciously replaced by a leaded frame of the same weight, shuttered if necessary by a plastic sheet that is transparent to gamma rays. This makes it possible to preserve the equilibrium of the standard gamma camera used. If the gamma camera is round, the frame is round. If the gamma camera is rectangular, the frame is rectangular. The leaded frame fulfills above all the role of a field shutter reducing the detection area to the useful zone and then enabling the counting rate of the gamma camera to be used in the revealing of the effective phenomena.

With the device of the invention, a high image resolution is achieved, related to the instrinsic quality of resolution of the detector without collimation. This is also due to the enlarging effect of the conical geometry related to the selected proximity of the gamma ray source. Thus, despite the aberrations related to this three-dimensional conical geometry, a better result is obtained.

Furthermore, the use of a point source has been turned to advantage to make a radioactive source, the use of which will be, firstly, easy and without danger for the operators and, secondly, can be implemented without raising the other problems encountered in the prior art. Indeed the only sources that can be envisaged are liquid sources. The fact of shifting the source dictates the need to manage the position of an air bubble that shifts depending on whether the source is placed beneath the gamma camera or above it, and on whether it is turned upside down or not. In the invention, the point source is made by means of a syringe that is filled and then partially emptied, in plunging its end into a jar, and in expelling the air bubble by reinjection into the jar. In this way, the syringe no longer has any air bubble. The position of the center of gravity of the radioactive source is then kept fixed in relation to the syringe, irrespectively of the orientation of this syringe (whether it is oriented upwards or downwards).

SUMMARY OF THE INVENTION

An object of the invention, therefore, is to provide a scintillation device comprising a gamma camera that can be used to measure the attenuation by transmission, through a body to be examined, of a gamma radiation emitted by a radioactive point source kept in a state of correspondence with a detector of said gamma camera, said detector being deprived of a collimator and being placed on a first side of the body, opposite in relation to another side of the body where the point source is placed, said body being shifted by a relative rotational motion with respect to the assembly formed by said point source and said detector, wherein said gamma camera is mounted on a movable structure, this structure being capable of making the detector of the gamma camera rotate in a vertical plane about the body positioned in an elongated position on a horizontal support, and wherein this structure also carries along the point source of gamma radiation, and means to weight the measured attenuation as a function of the source-detector distance and as a function of the plane character of the detector.

BRIEF DESCRIPTION OF THE DRAWINGS

The invention shall be understood more clearly from the following description and from the appended figures. These are given purely by way of an indication and in no way restrict the scope of the invention. The figures show:

FIG. 1 gives a schematic view of a gamma camera according to the invention;

FIG. 2 shows an embodiment of a radioactive source according to the invention;

FIG. 3 shows a diaphragm to limit the field of the gamma camera to an area smaller than the projected area of the body;

FIG. 4 shows a schematic sectional view of the weighting done.

MORE DETAILED DESCRIPTION

FIG. 1 shows a scintillation device according to the invention. This device comprises chiefly a gamma camera 1 provided with its scintillator (not shown), an array 21 of photomultiplier tubes of its detector D and an assembly for the processing 2 and display 3 of emission images acquired by the gamma camera 1. The detector of the gamma camera is capable of rotating about the body of a patient (not shown) placed on a patient-bearing board 4. To this end, the detector of the gamma camera is held by a supporting stand 5 through an arm-shaped structure 8. The structure 8 can rotate in the direction indicated by the arrow 6 about a horizontal axis 7. This enables the detector of the gamma camera 1 to rotate in a vertical plane about the horizontal axis 7. The arm 8 is, firstly, fixed to the detector of the gamma camera 1 and, secondly, can rotate, in being driven by a motor (not shown) about the axis 7.

The board 4 and the supporting stand 5 are kept facing each other by pedestals 9 and 10 respectively. The pedestals may be movable with respect to each other to shift the body before the detector.

The scintillation device of the invention also includes a radioactive source 11 considered to be a point source and located within a protective chamber 12. The protective chamber 12 is designed to protect the operators from the radioactive rays emitted throughout space by the source 11. The chamber 12, which is made of lead for example, is thus provided on one side facing the detector of the gamma camera 1 with a hole by which the rays emitted by the source 11 can be propagated. The source 11 is shown in FIG. 2. On the side opposite its hole, the chamber 12 may include an aperture capable of being shuttered, enabling the introduction of the radioactive source into the interior.

The chamber 12 is kept fixedly joined to the gamma camera 1 by a gibbet arm 13. The arm 13 is fixed to the detector D by being engaged in a set of slideway elements 14 and 15 fixed to this detector. The arm 13 then rises substantially perpendicularly to the plane of the detector D. The arm 13 is collapsible and has a forearm 16 which may penetrate into the base 50 of the arm 13. The forearm 16 is ended in extension by a pivot 51 on which a telescopic swing-bar 52 is mounted, in a rotationally free state, perpendicularly to the axis of the pivot. At its end opposite the pivot, the swing-bar 52 bears a ring 53 designed to receive the chamber 12 in an internal sliding movement. The telescopic character of the arm 13 and of the swing-bar 52 as well as the rotation about the pivot 51 and the sliding of the chamber 12 enable the source to be given any chosen position in space relative to the detector D.

The detector D is surmounted by a frame 17. The frame 17, made of lead for example, preferably has the same external dimensions as a collimator 18 of the gamma camera which has been temporarily removed. It has the same shape. If the collimator is round, the frame is round, and if the collimator is rectangular, the frame is rectangular. The frame 17 also has fixing devices, for example using screws 19 which occupy exactly the same positions and fit into one another in exactly the same way as do the fastening devices 20 of the collimator 18 on the gamma camera 1. The frame 17 is placed on the periphery of the array 21 of photomultiplier tubes of the detector of the gamma camera 1. These photomultiplier tubes are shown symbolically herein because they are actually not visible (the are masked by the presence of the scintillator which is always necessary). The array of these tubes may round, hexagonal or even rectangular. The tubes themselves may have a round, hexagonal or square section.

The frame 17 therefore has a hollowed internal part capable of letting through the gamma radiation. To prevent the interior from being polluted by dust or, more simply, to make it easier to handle the frame 17, this frame may be provided, in its interior, with a plate made of transparent plastic. Since it is sought to use standard machines, the frames 17 are preferably made so that their weight is as close as possible to the weight of the collimator 18 that they are supposed to replace. The result of this will be that the rotational motion of the gamma camera 1 about the axis 7 will not be disturbed.

The fact that the arm is engaged in the slideway elements gives the gamma camera great universality: without the arm, the gamma camera becomes a standard machine again.

FIG. 2 shows a syringe 22, for example made of glass or plastic. This syringe has a body 23 and a piston 24. The body 23 is provided with a hole 25. In one example, the hole 25 has a protuberance provided with a thread 26. The protuberance 25 may thus be screwed into the corresponding part of a hollow rod 27 that plunges into a jar 28. The jar 28 is preferably made of lead. It may be opaque. The rod 27 is held in the jar 28 by a stopper 29. The jar contains a dilution of radioactive product, preferably the same product as the one that can be injected into the patient. In view of the capillarity of the liquids that have to be conveyed from the jar to the syringe 22, the diameters of the rod 27 and of the hole 25 are such that they naturally counter the flow of the fluid 30 contained in the bottle 28.

The following is the filling mode. The bottle is positioned normally on its bottom 31, the syringe 22 is screwed on to the rod 27 and the piston 24 is raised so that the syringe gets filled. Once the filling is done, the unit formed by the jar 28 and the syringe 22 is then overturned so that the jar is now positioned above the syringe. When this is done, air bubbles 32 that would have remained in the syringe 22 take up position close to the hole 25: they are the first to be expelled as soon as the piston is pushed. The piston 24 is then pushed until it occupies a pre-determined position 33 in relation to the body 23. While this is being done, it is seen to it, firstly, that the quantity of fluid 30 in the syringe is always the same and, secondly, that the air bubbles have disappeared. Then, the activity of the source is measured in an activimeter, and the volume of liquid in the syringe is adjusted, in repeating the same operations so as to obtain the desired activity.

This is important for, in the invention, the patient lies still on the board 4 and the gamma camera 1 rotates about him. Consequently, the source 11 takes up vertical positions, either above or beneath the patient. If no care is taken, the position of the bubbles such as 32 would falsify the position of the center of gravity of the radioactive liquid contained in the syringe and hence the position of the focal point of emission.

FIG. 3 shows a frame 17 provided with its anchoring devices 19 and a diaphragm 34 with flaps. Herein, this diaphragm has two sets 35 and 36 of flaps, enabling the field of the gamma camera seen by the source 11 to be reduced. This makes it possible to prevent the saturation, by an excessive quantity of energy coming directly from the source 11, of those regions of the detector of the camera which may not be located in the image, projected on this camera, of the body to be studied. For example, the patient's head, if placed before the gamma camera, will not mask the entire field of the camera. The unmasked parts would otherwise receive direct radiation. In a preferred way, the diaphragm does not work with symmetrical movement. On the contrary the flaps, in at least one direction, for example the direction 36 (FIGS. 1 and 3) are designed to leave an aperture on the edge of the plane of the detector rather than at its center. In this way, lateral parts, not hatched and at a distance from the supporting stand 5 of the detector D, are for example active in detection. As a consequence, the support 4 may be shifted in the direction of the arrow 60 so that only the patient's head is placed beneath the detector D of the gamma camera. The rest of the detector D is then in an overhanging position with respect to the head. In this case, the arm 8 of the structure, which is telescopic, may be made to re-enter its leg 61 so that the detector comes as near as possible to the patient's head, in practice to within a few centimeters of his nose. Under these conditions, the detector is then closer to the head than if it had to circumvent the patient's belly which is naturally more bulky. For this very same purpose, the board 4 is also less wide at 62, where the patient has to lay his head, than at the position where he has to lay his trunk. This results in better resolution owing to the fact that the detector can be placed closer to this patient's body.

Besides, given the greater sensitivity of the gamma camera when it has no collimator, it is possible to narrow the energy window and select the detected photons. This makes it possible to reduce the effects of the scattering without in any way causing a loss of homogeneity of the gamma camera. Indeed, the scattered photons have lower energy. The scattered photons detected in the absence of collimation falsify the result of the detection since their directions and their paths in the detector are completely random and arbitrary. In the invention, since there are many photons, it is possible to be more demanding with respect to the photons taken into account and to consider only those whose energy corresponds precisely, with a low range, to the energy emitted by the source. To this end, the range of detection of the processing means 2 is programmed with a setting button 37. In the invention, the detection range is reduced to less than 10%, that is to say approximately 5%, of the nominal value of the energy to be detected. It will be recalled that in standard detection of emission, the range is of the order of 20% of the nominal value of the energy.

The weighting correction in question for taking into account the conical geometry of acquisition is due to the plane character of the detector. It is as follows. The line 4 shows a sectional view of the detector D, with a center D' located at a distance SD from the source 11. The detector is seen from the source 11 at a constant angle $\Theta$. The rays that reach the detector on its straight lateral edge 70 form, for a given direction of acquisition, an angle $\Phi$ with an axis OY having a reference OXOY. The reference OXOY passes through the center of rotation of the gamma camera. The center of rotation is placed on the axis 7. The angle $\Phi$ characterizes the direction of projection. The projection of a sampled sector $\delta\Theta$ on the detector D occupies an area, on this detector, that depends on the divergence, in relation to a mean direction SO of irradiation, of the detection position. In the invention, the measurement made is corrected by weighting, at each position of the detector, by means of a coefficient that takes account of the attenuation prompted by each occupation of a surface area. The reverse of the coefficient can be written as follows for the projection of a sector $S_1$ contiguous to the mean direction SO.

$$a_1 = SD.\tan\delta\Theta$$

For a following sector, it can be written as follows:

$$a_2 = SD. (\tan 2\delta\Theta - \tan \delta\Theta).$$

For a detector corresponding to an even more shifted sector distance, it can be written:

$$a_i = SD. (\tan i\delta\Theta - \tan (i-1) \delta\Theta).$$

The measured values are corrected as a function of these coefficients. This method enables the use of a known algorithm of reconstruction whereas the proximity of the source combined with the plane character of the detector countered it. In doing so, standard reconstruction algorithms are used (with no specific development) and above all it is possible to approach the source 11, thus making the device easy to handle whereas it cannot be handled if the source has to be at a distance.

It will be noted that the weighting correction can be done in taking account of the deviation with respect to the mean direction measured along one direction (35) and also along the other direction (36). With the deviation measured along only one direction, the correction is already sufficient to eliminate a "bowl" effect in the reconstruction of the coefficients of attenuation in transmission.

With respect to the reconstruction proper of the coefficients of attenuation on the basis of the measured and corrected detection values, the algorithms applied are either reconstruction algorithms of a parallel type with a rearrangement of projections or reconstruction algorithms of a flat fan beam type without rearrangement. For example, for the latter, the algorithm could be of the type described by P. LEWITT in "Computerized Tomography with Fan Beam Geometry", *Journal of Computer Assisted Tomography*, 1 (4) 1977, or again of the type described by S. Webb, Sutcliffe, Burkinshaw, Horsman: "Tomography EC Reconstruction From Exponentially Obtained Fan Beam Projection", *IEEE Transactions on Medical Imaging*, Vol. MI-6, No. 1, March 1987. A known type of standardization logarithm is also done on the measured values. This standardization logarithm relates, rather than to the coefficients themselves, to the manipulation of the logarithms of the attenuation coefficients. This simplifies the computations. This standardization logarithm is furthermore known.

Besides, the fact that the irradiation is totally conical is overlooked so as to liken it to an irradiation in the form of a pancake segment. The weighting done is sufficient not to be hampered by this approximation.

With the gamma camera of the invention, about sixty half-shots on one half rotation can be done in one minute. These approximately sixty shots can be used to determine the coefficient of absorption of the gamma radiation within the body in volume elements, the dimensions of which are of the order of 5 millimeters by 5 millimeters. Once these coefficients of absorption have been acquired, a correction is made, according to known techniques, of the tomography images obtained by emission and in which the transmission attenuation had been considered to be zero. A correction mode such as this has been described, for example, in the first article cited here above.

What is claimed is:

1. A scintillation device comprising a gamma camera that can be used to measure the attenuation by transmission, through a body to be examined, of a gamma radiation emitted by a radioactive point source kept in a state of correspondence with a detector of said gamma camera, said detector being deprived of a collimator and being placed on a first side of the body, opposite in relation to another side of the body where the point source is placed, said body being shifted by a relative rotational motion with respect to the assembly formed by said point source and said detector, wherein said gamma camera is mounted on a movable structure, this structure being capable of making the gamma camera rotate in a vertical plane about the body positioned in an elongated horizontal position on a support, and wherein this structure also carries along the point source of gamma radiation, and means to weight the measured attenuation as a function of the source-detector distance and as a function of the plane character of the detector.

2. A device according to claim 1, wherein the detector of the gamma camera is provided with a removable frame placed on the rim of the detector.

3. A device according to claim 2, wherein the frame includes a diaphragm to reduce the field of the gamma camera seen by the point source.

4. A device according to claim 2, wherein the frame has a weight substantially equal to the weight of the absent collimator.

5. A device according to claim 3, wherein the diaphragm possesses flaps with dissymetrical movement.

6. A device according to any of the claims 1 to 5, wherein the point source is contained in a syringe.

7. A device according to claim 6, comprising a jar provided with a hollow rod plunging by one end into the jar and provided, at its other end, with a receptacle to receive a hole of the syringe.

8. A device according to any of the claims 1 to 5 comprising, in means for the processing of the detected signal, means to reduce the detectable energy range to less than 10% of the nominal value of the energy of the gamma photons to be detected.

* * * * *

UNITED STATES PATENT AND TRADEMARK OFFICE
CERTIFICATE OF CORRECTION

PATENT NO. : 5,359,198
DATED : October 25, 1994
INVENTOR(S) : Michel BOURGUIGNON, et al.

It is certified that error appears in the above-indentified patent and that said Letters Patent is hereby corrected as shown below:

On the title page, Item [30], the PCT Information has been omitted from the Foreign Application Priority Data, please insert:

--Jul. 24, 1990 [PCT] PCT.....PCT/FR90/00560--

Signed and Sealed this

Eleventh Day of April, 1995

Attest:

BRUCE LEHMAN

*Attesting Officer*      *Commissioner of Patents and Trademarks*